United States Patent [19]

Hon et al.

[11] 4,252,131

[45] Feb. 24, 1981

[54] CATHETER FOR MEASURING INTRAUTERINE PRESSURE

[75] Inventors: Edward H. Hon, Bradbury, Calif.; Carmelo Dali, Cheshire, Conn.

[73] Assignee: American Home Products Corporation, New York, N.Y.

[21] Appl. No.: 896,774

[22] Filed: Apr. 17, 1978

[51] Int. Cl.³ .............................................. A61B 17/42
[52] U.S. Cl. ................................. 128/748; 128/673; 128/349 R; 73/706
[58] Field of Search ....... 128/2 R, 2 M, 2 W, 2.05 D, 128/348, 349 R, 350 R, 351, 343, 341, 240, 241, 361, 263, 214; 73/756, 731, 706

[56] References Cited

U.S. PATENT DOCUMENTS

| | | | |
|---|---|---|---|
| 2,845,930 | 8/1958 | Brown | 128/348 |
| 3,095,871 | 7/1963 | Mann et al. | 128/344 |
| 3,157,201 | 11/1964 | Mann | 128/2.05 D |
| 3,380,448 | 4/1968 | Sadove | 128/348 |
| 3,559,643 | 2/1971 | Pannler, Jr. | 128/214.4 |
| 3,581,733 | 6/1971 | Grandjean | 128/2.05 D |
| 3,877,429 | 4/1975 | Rasumoff | 128/214.4 |
| 4,023,559 | 5/1977 | Gaskell | 128/2 W |
| 4,030,481 | 6/1977 | Hill | 128/350 R |
| 4,136,681 | 1/1979 | Hon | 128/2 R |

OTHER PUBLICATIONS

"Obstetrics", Taylor, Williams & Wilkins Co., Baltimore, Md., 1972, pp. 95-96.

Primary Examiner—Robert W. Michell
Assistant Examiner—J. L. Kruter
Attorney, Agent, or Firm—Darby & Darby

[57] ABSTRACT

A catheter is disclosed for measuring the intrauterine pressure of a woman in labor. It comprises an elongated flexible tube filled with liquid and having one end apertured to permit the liquid therein to communicate with bodily fluids in the uterus; the other end is sealed by a relaxed diaphragm. The catheter tube is inserted into a curved guide tube which is scored at the end adjacent the apertured end of the catheter to permit the catheter to be extended from the guide tube. The guide tube is also scored along its length to permit a portion of the wall of the guide tube to be peeled away leaving a longitudinal slot through which the catheter can be passed after insertion into the uterus. The catheter and guide tube are disposed in a liquid-tight envelope, the open end of which is sealed about the catheter to prevent escape of the liquid within the catheter. A leg plate for supporting a pressure transducer includes means for removably connecting the catheter to the transducer and means for removably attaching the leg plate to the skin of the patient.

8 Claims, 9 Drawing Figures

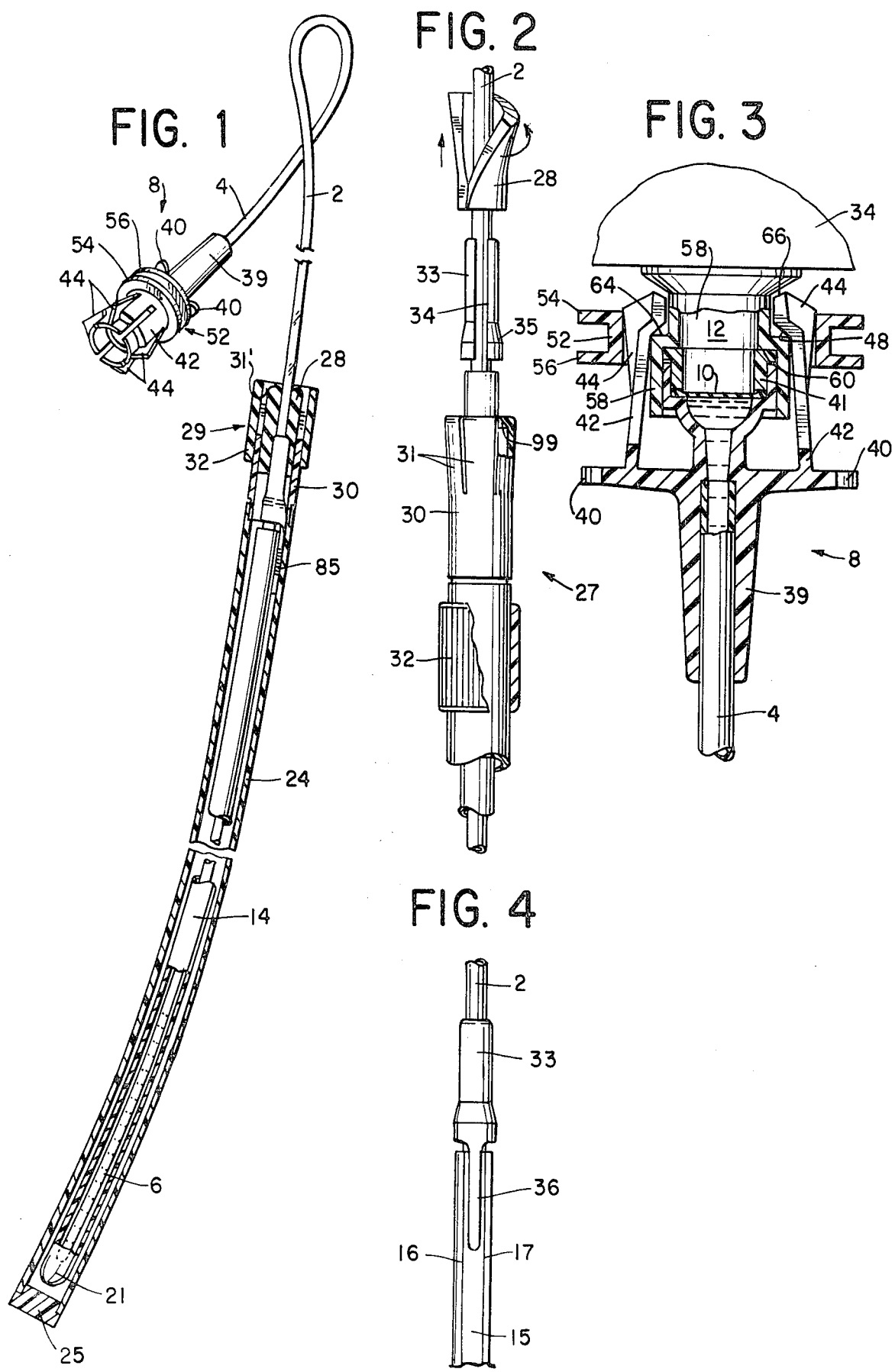

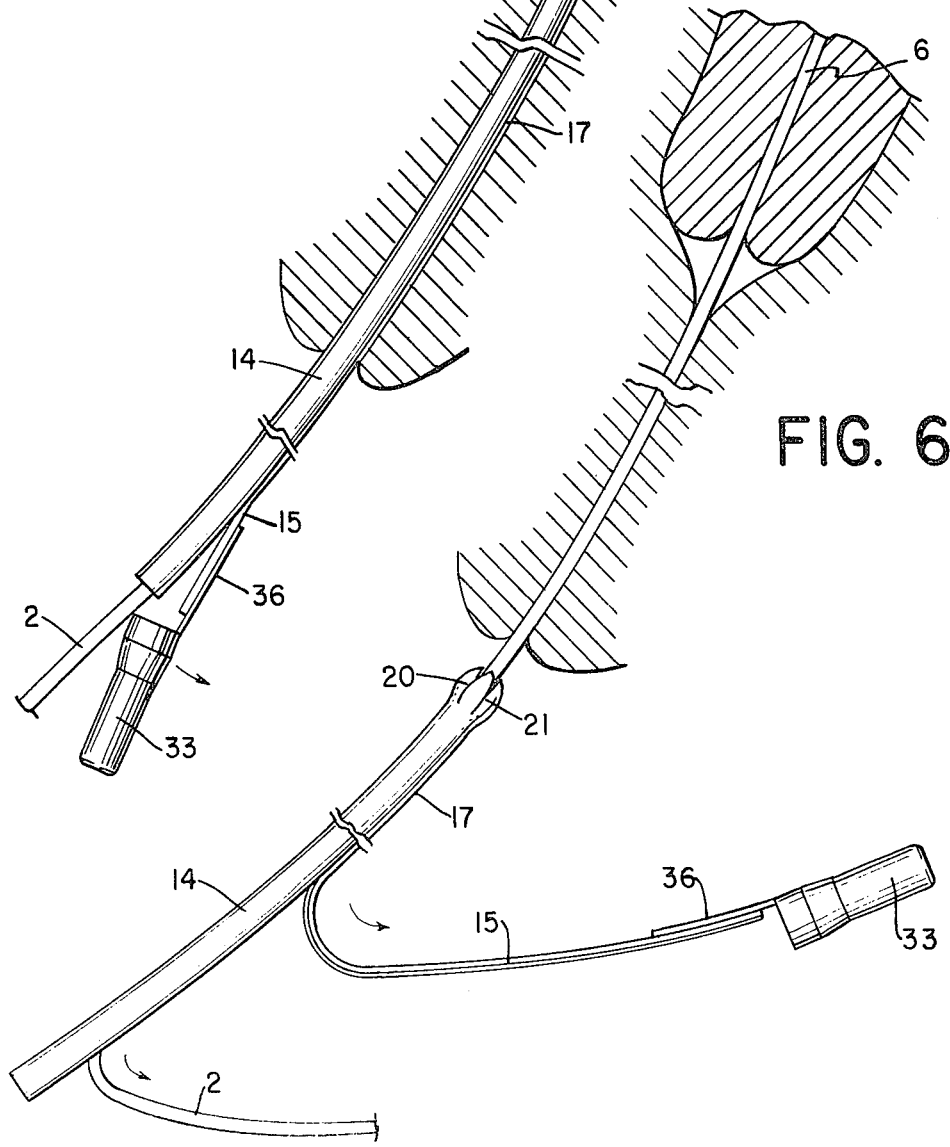

CATHETER FOR MEASURING INTRAUTERINE PRESSURE

BACKGROUND OF THE INVENTION

This invention concerns the measurement of pressure within a body cavity. More specifically, this invention pertains to a catheter adapted to be used for the measurement of intrauterine pressure during labor.

Fetal monitoring is a standard procedure for monitoring the condition of a fetus during childbirth. In most cases, fetal heart rate and intrauterine pressure are measured and separately plotted on a strip-chart recorder. By examining the plotted curves, the onset of certain distress conditions can be detected so that appropriate remedial action can be taken earlier than would otherwise be possible.

To measure intrauterine pressure a catheter may be inserted into the uterus and filled with liquid so that the force of the intrauterine contractions can be transmitted through the uterine fluids and the liquid in the catheter, to a pressure-measuring device such as a strain gauge or the like.

In prior art applications of intrauterine catheters of the type described, a cumbersome procedure is required to fill the catheter with liquid and then couple the catheter to the strain gauge to complete a liquid path or column from the uterus to the gauge. Conventionally, the catheter is inserted through a relatively rigid guide tube which is curved to conform to the vaginal canal. The catheter is pushed through the guide tube until the uterine end of the catheter is located correctly within the uterus. The liquid is injected by means of a syringe and suitable adaptor into the catheter. It is then necessary to slide the guide tube off the catheter which requires removal of the adaptor and syringe through which the liquid was injected into the catheter.

After the guide tube has been removed, the catheter is coupled by means of the adaptor to a three-way stopcock, with the other inlets of the stopcock being connected, respectively, to the luer fitting of the strain gauge and the syringe. This enables the bleeding of air which is likely to enter the system during insertion of the catheter into the uterus. The bleeding operation requires first that water be again injected into the catheter. The catheter is then closed by the stopcock and the syringe used to inject water into the strain gauge dome until all air is removed. Next, the syringe is removed to obtain a "zero" setting by opening the strain gauge (after the air bubbles have been removed) to atmosphere. The "off" lever on the three-way stopcock is then rotated so that the catheter is coupled directly to the strain gauge.

During insertion, known intrauterine catheters of the type described may be "plugged" by materials within the vaginal canal. If this happens, pressure measurements are no longer meaningful and the catheter must therefore be cleaned which invariably requires that the system be again bled as described above.

Even if a sterile liquid is used, when the liquid injection and air bleeding procedures take place in an insterile environment, use of these standard catheters can be accompanied by substantial risk of infection.

One approach to solving the aforementioned problems is disclosed in U.S. patent application Ser. No. 658,821 (now U.S. Pat. No. 4,136,681), which is assigned to the assignee of this application. U.S. Pat. No. 4,136,681 discloses a prefilled catheter sealed on one or both ends by a limp membrane through which uterine pressure is transmitted to a strain gauge or other suitable measuring device. The catheter is packaged in a longitudinally slit guide tube and sealed by a film to prevent the sterile fluid in the catheter from escaping. The film must be punctured to permit entry of the catheter into the uterus and must be torn along its length to permit removal of the guide tube from around the catheter. The principal drawback of the device is that it is relatively difficult and expensive to manufacture.

The main object of the invention is to provide an intrauterine catheter which is easier to use than the catheters currently in use. A more specific object of the invention is to provide a low cost, disposable catheter for measuring uterine pressure which does not have to be bled of air at the time of use.

SUMMARY OF THE INVENTION

Briefly, the invention comprises a guide tube and an elongated catheter having a gauge end adapted to be connected to a transducer and a maternal end adapted to be inserted through the vagina and cervix of a woman and into her uterus. The guide tube, which is less flexible than the catheter, is adapted to be inserted into the vaginal canal to provide a conduit for the catheter and is scored along its length to permit a portion of the wall of the guide tube to be peeled away after use, leaving a longitudinal slot through which the catheter can be passed. A sleeve positions the catheter within the guide tube during transit and storage and the combination is packaged within a sealed enevelope. The catheter is prefilled with a sterile liquid, the gauge end of the cather terminating in a connector assembly including a diaphragm which seals the catheter and which transmits pressure fluctuations to a suitable transducer.

DESCRIPTION OF THE DRAWINGS

FIG. 1 is a perspective view of a part of the apparatus of the invention with some components in section.

FIG. 2 is a partially sectioned front view of part of the apparatus of the invention shown in FIG. 1.

FIG. 3 is a sectioned plan view showing another part of the apparatus of the invention in FIG. 1.

FIG. 4 is a rear view of part of the apparatus shown in FIG. 2.

FIG. 5 is a view of the apparatus of the invention in one stage of use in its intended environment.

FIG. 6 is a view of the apparatus of the invention in another stage of use in its intended environment.

DESCRIPTION OF THE PREFERRED EMBODIMENT

Figure 7:
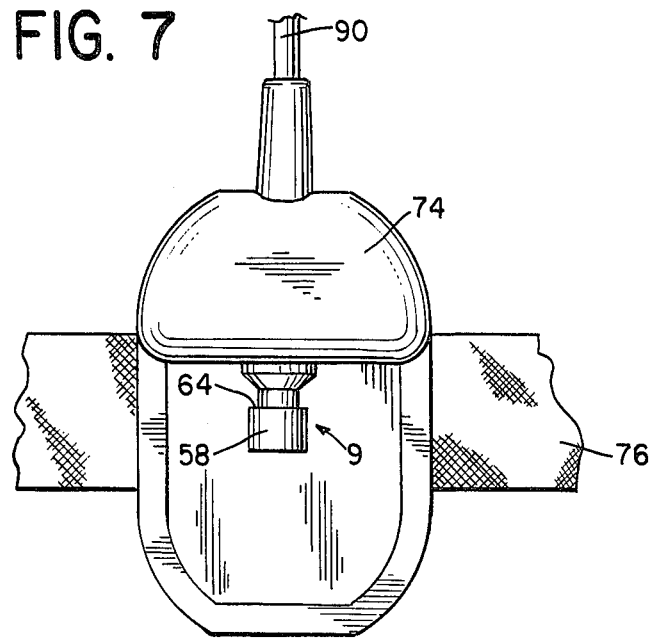
FIG. 7 is a plan view showing an additional part of the apparatus of the invention in relation to part of the apparatus of the invention shown in FIG. 3.

Referring now to the drawings, there is shown a hollow elongated flexible catheter 2 having a gauge end 4 and a maternal end 6. The catheter 2 includes a multiplicity of pinholes 7 on its cylindrical surface to permit a fluid (e.g. distilled water), with which the catheter is filled, to communicate with the bodily fluids inside the uterus. For example, one hundred pin holes 7 may be formed in the catheter wall starting one inch from end 6 and extending about ten inches up the catheter wall. The gauge end 4 of the catheter 2 terminates in a connector assembly 8 which serves to attach the gauge end of the catheter 2 to a transducer 9 (FIG. 3).

The liquid column in catheter 2 is closed at the gauge end by a pressure transmitting diaphragm 10 within connector assembly 8 (FIG. 3). The diaphragm 10 can be made of a thin plastic layer or a thin material including several layers of lamination composed of one or more plastics. The thickness of the diaphragm preferably is on the order of 0.001 inches or less in order to enhance pressure transmission from the liquid within the catheter 2 to the forward surface of the transducer 9 shown in FIG. 3. Diaphragm 10 should transmit pressure fluctuations to transducer 12 with minimal energy absorption.

In assembling the apparatus of the invention, the catheter 2 is disposed within a hollow elongated guide tube 14 which is formed with a curve conforming generally to the anatomical curvature of the vaginal canal of a woman. The guide tube 14 is preferably made of a material which permits it to be form-sustaining, that is, to maintain its curvature, but is pliable enough so that, during insertion through the vaginal canal, the guide tube may have its curvature temporarily altered by forces exerted upon it thereby minimizing discomfort to the patient. A suitable plastic having the aforementioned form-sustaining properties can be used.

The wall of the guide tube 14 is scored along its length as at 16 and 17 (FIG. 4) to permit the portion 15 of the guide tube wall between score lines 16 and 17 to be peeled away in a strip leaving a slot running the full length of the guide tube wall. The inner diameter of the guide tube 14 is greater than the outer diameter of the catheter 2 permitting the catheter 2 to slide within the guide tube 14. The distance between the score lines 16 and 17 is large enough to permit the catheter to be passed through the slot left in the guide tube wall to separate the guide tube from the catheter.

In addition to the scorelines 16 and 17 which run the full length of the guide tube 14, scoring can be provided, as at 20 and 21 in FIG. 6, running a short distance radially from the tip of the maternal end of the guide tube 14. The score lines 16, 17, 20 and 21 define between each adjacent pair thereof a pliable finger-like prong member yieldable away from the axis of the guide tube 14. When the maternal end of the catheter 2 is forced against the maternal end of the guide tube 14, it causes the guide tube 14 to split along a length of the score lines 16, 17, 20 and 21. Complete separation, however, does not occur at portions of the score lines 16 and 17 rearward of the maternal end of guide tube 14 until the guide tube wall portion between score lines 16 and 17 is peeled away in a manner to be described.

In the preferred embodiment of the invention, score lines 16 and 17 serve the dual purpose of weakening the maternal end of the guide tube 14 for penetration by the maternal end of the catheter 2 and of weakening the side wall of the guide tube 14 to permit the guide tube 14 to be removed from about the catheter 2. Separate scoring lines can be provided for the penetration and removal functions. Preferably, score lines 16 and 17 are wedge-shaped in cross-section, extending through about 80% of the thickness of the wall, and formed during extrusion of the guide tube 14. Score lines 20 and 21 may be cut after the tube has been closed at the uterine end.

At the time of manufacture, the catheter 2 is inserted into substantially the full length of the guide tube 14, as seen in FIG. 1. To ensure the liquid-tight integrity of the prefilled catheter 2 and guide tube 14 during shipment and storge prior to use, an outer tubular sheath or envelope 24 receives the catheter 2 within the guide tube 14 and the entire assembly is filled with liquid as described below. The envelope 24 is sealed at its maternal end by a plug 25. The gauge end of the envelope 24 is provided with a sealing means 29 which can be released to permit the envelope 24, guide tube 14 and catheter 2 to be filled with liquid at the time of manufacture. The sealing means 29 can then be tightened as explained below to form a liquid-tight seal between the envelope 24 and catheter 2 to prevent liquid within the envelope 24 from spilling.

In the preferred embodiment of the invention shown in FIG. 1, the envelope 24 is made of a rigid material such as a hard plastic. The tubular envelope 24 is fitted at its gauge end with a cylindrical retaining member 30 which is made of a resilient plastic and is slotted about a portion of its circumference to form yieldable fingers or prongs 31 (FIG. 2). A hollow elastomeric plug 28 is disposed about the circumference of the catheter 2 and compressibly fitted into the cylindrical member 30 urging the prongs 31 to spread outwardly away from the axis of the tubular envelope 24. The prongs 31 can have radially inward extending ridges 31 to prevent axial movement of the elastomeric plug when the prongs are urged inwardly. The plug 28 has an axial slot in its slide wall to facilitate its removal from the catheter 2 after withdrawal from the envelope 24. A cylindrical friction collar 32 of inner diameter only slightly greater than the outer diameter of the envelope 24 is slid onto the maternal end and then along the length of the envelope 24 until brought into compressing engagement with the prongs 31 thereby forcing the prongs 31 inwardly and compressing the elastomeric plug 28 between the prongs 31 and the exposed area of the catheter 2 to form a liquid tight seal and also to prevent relative axial movement between the catheter 2, guide tube 14 and envelope 24.

A sleeve 33 is removably fixed to the catheter 2 and the guide tube 14 at the time of manufacture. Sleeve 33 is axially slit at 34 and terminates at its maternal end in a bell-like portion 35 having an enlarged circumference. Extending from the widened portion 35 is an elongated tab 36 which is affixed to the outer wall of the guide tube 14 between score lines 16 and 17. Bonding between the tab 36 and the guide tube 14 may be acomplished by the application of a suitable adhesive or by a heating process as will be known to those skilled in the art.

The inner diameter of the sleeve 33 forms a force fit with the outer diameter of the catheter 2. Moreover, the sleeve 33 is made of a resilient material such as a pliable plastic so that the catheter may be forced into and out of the sleeve 33 through the slot 34. The sleeve 33, therefore, releasably grasps the portion of the catheter 2 which extends from the gauge end of the guide tube 14, and is firmly attached to the removable strip in the guide tube wall between score lines 16 and 17.

Referring now to FIGS. 1 and 3, the connector assembly 8 includes a collar 39 from which four mutually orthogonal flat projections 40 extend in a plane transverse to the axis of the end portion 4 of the catheter. Extending axially beyond the plane of the projections 40 from the collar 39 is a cylindrical portion followed by a hollow hemispherical dish-like portion terminating in a stepped cylindrical ring of widened outer diameter and having an inner circular shoulder which receives a flanged ring 41 to seal the diaphragm 8 in place. Extending from the projections 40 are respective circumferential prongs 42 on which there are formed integral fins which have outer surfaces 44, respectively, and in the interior of which there are inward sloping grasping surfaces 48, respectively. Slidably mounted about the prongs 42 for longitudinal movement along an axis extending from the catheter 2 there is a locking nut 52 having a grasping portion in the shape of two annular flanges 54 and 56 on its exterior and a hollow cylindrical interior. The grasping flanges 54 and 56 extend radially from the locking nut 52 to enable the nut 52 to be slid over the surfaces 44 of the prongs 42 when the connector assembly 38 is attached to the transducer 12.

As the nut 52 is slid over the prongs 42, it exerts inward pressure on the surfaces 44 forcing the prongs 42 inwardly to grasp the transducer housing.

The transducer 12 is housed in a cylindrical enclosure about which there is mounted a stepped ring 58 having a large outer diameter at its maternal end and a smaller outer diameter at its gauge end thereby forming an outer circular shoulder 64 and an inner circular rim 60. When the diaphragm 10 is in intimate contact with the surface of transducer 9, a portion of the inward grasping surfaces 48 of the prongs 42 is in radial allignment with the shoulder 64 of the stepped ring 62. The rim 60 limits insertion so that when the flanged ring 41 abuts it, the diaphragm 10 is in intimate engagement with the transducer 12.

The ends of the prongs 42 are provided with additional cam surfaces 66 to cause the prongs 42 to be spread apart as the cylindrical collar 38 is slid over the stepped ring 62.

To disengage the catheter from the transducer the nut 52 is slid toward the maternal end of the catheter 2 thereby releasing the prongs 42 so that the catheter 2 with collar assembly 38 and nut 52 may be axially displaced from the transducer 12 until complete separation is achieved.

When it is desired to apply the catheter to a patient, the friction collar 32 is displaced by turning it and sliding it axially toward the maternal end of the envelope 24 thereby relieving the pressure on the prongs 31 of the retaining member 30. The catheter-guide tube assembly may then be withdrawn from the envelope 24 with the enlarged plortion 35 of sleeve 33 pulling the hollow elastomeric plug 28 with it. The elastomeric plug 28 can then be removed via the slit in its wall (see FIG. 2) and discarded with the envelope 24 and friction collar 32. The catheter-guide tube assembly may then be inserted through the vaginal canal of the patient and the catheter extended into the uterus and the guide tube removed as will later be described.

Referring to FIGS. 5 and 6, to insert the catheter 2, it and the guide tube 14 are gently pushed into the vagina and through the vaginal canal until the physician feels that the maternal end of the guide tube is adjacent the cervix (FIG. 5). The slotted sleeve 33 is then pulled away from the catheter 2 and the catheter 2 is pushed forward causing the maternal end of the guide tube 14 to split at score lines 16, 17, 20, and 21. The catheter 2 can then be pushed through and beyond the guide tube, with its maternal end 6 penetrating the cervix and entering the uterus (FIG. 6). The guide tube 14 is then axially pulled along the catheter from the vaginal canal with one hand while the catheter is maintained in position with the other until the maternal end of the guide tube clears the vagina. The strip 15 between score lines 16 and 17 can then be peeled from the guide tube 14 and discarded leaving a slot in the guide tube 14.

Still holding the catheter in place with one hand the physician then pulls the catheter 2 through the slot in the guide tube 14 and continues this motion until the guide tube 14 is fully removed from about the catheter 2. The fluid-filled catheter 2 remains in proper position in the uterus. The connector assembly 8 at the gauge end of the catheter 2 can be connected to the transducer 9 before or after insertion of the catheter 2 into the patient. The transducer 9 is electrically wired to a fetal monitor or other electrical device suitable to display or analyze the uterine pressure information carried by the electrical signals from the transducer.

There is shown in FIG. 7 a leg plate 74 which can be attached by conventional means to a belt 76 adapted to be fastened about the leg, preferably at the thigh, of a woman in labor. Mounted on the leg plate is the transducer 9 for generating a pressure responsive electrical signal in a well-known manner. The belt 76 is preferably made of a foam-like material for comfort. Instead of a belt, an adhesive backing may be employed on a leg plate 74' as shown in FIGS. 8 and 9 to adhere to the skin on the leg of the woman.

Figure 8:
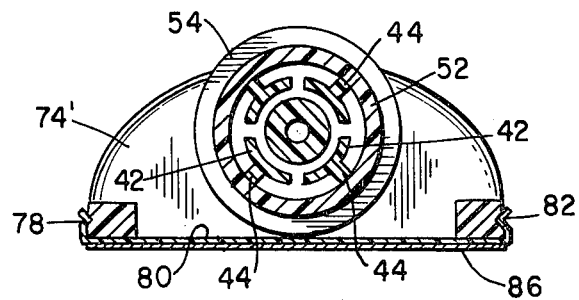
FIG. 8 is a sectional elevation of a modified form of the apparatus of FIG. 7.
Figure 9:
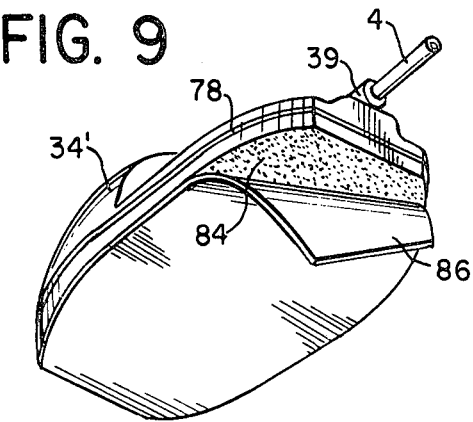
FIG. 9 is a perspective view of the apparatus of the invention shown in FIG. 8.

The leg plate 74' can be grooved about its periphery as at 78 in FIG. 8 to receive a detachable lower plate 80 adapted to mate with the undersurface of the leg plate 74' and having a circumferential lip 82 which is provided with a tongue adapted to be received by the groove 78 thereby permitting the plate 80 to be snapped onto and off of the underside of the leg plate 74'. The undersurface of the plate 80 is coated with an adhesive 84 to which there is applied a protective backing 86 having a lesser affinity for the adhesive 84 than does the undersurface of the plate member 80.

To attach the leg plate 74' to the leg of the patient, preferably at the thigh, the backing 86 is peeled from the plate 80 which is attached to the leg plate 74' and the leg plate 74' is pressed onto the patient's leg. After monitoring is completed, the leg plate 74' can be separated from the plate 80 which can then be discarded.

Extending from the transducer 12 is a cable 90 (FIG. 7) which includes wires suitable for transmitting the electrical signals generated by the transducer 9 in response to the pressure exerted on its front surface and applying the electrical signals to a fetal monitor or other electrical pressure display or measurement equipment to which the wires of the cable 90 are electrically connected. Hence, the length of the catheter 2 need only be sufficient to reach the leg of the patient and need not, as in prior catheters, be required to extend to the monitor or other electrical sensing apparatus. Keeping the catheter length short minimizes any undesirable pressure drop across the catheter 2 due to friction between the liquid therein and the interior of the catheter wall and thus enhances the sensitivity and accuracy of the pressure measurement system.

In manufacturing the catheter, the connector assembly 8 is secured to catheter 2 so that diaphragm 10 seals the gauge end of the catheter. The uterine end of catheter 2 is then inserted into guide tube 14 (with plug 25 in place as shown in FIG. 1) and the tab 36 of sleeve 33 adhesively or thermally fixed to the guide tube between score lines 16 and 17 as shown. The upper slotted end of sleeve 33 is then snapped on to the catheter tube as shown, the plug 28 positioned as shown in FIG. 1, and the catheter and guide tube inserted into envelope 24.

With collar 32 loosely engaging the upper portion of the retaining member 30, the entire envelope assembly is submerged in water and a vacuum is then applied to the unsealed (gauge) end of the envelope 24. The application of the vacuum causes all of the air within the envelope 24, guide tube 14, and catheter 2 to be evacuated so that when the vacuum is removed, the sterile water is pulled into the catheter, guide tube and envelope. After the device is filled with water, the collar 32 is then moved upwardly into the position shown in FIG. 1 to thereby seal the entire system. The article may then be packaged for shipment and storage until use.

Various different materials may be used to make the individual parts of the invention. Polyethylene is suitable for use as the catheter tube 2, the guide tube 14, envelope 24 and sleeve 33. Polypropylene may also be used as the material for envelope 24. The connector assembly 8 may be made from polycarbonate and the collar 32 may be made of Nylon. The plug 28 may be made of a silicone rubber.

Retaining member 30 and plug 25 are shown as parts separate from envelope 24; however, for production purposes it is contemplated that the envelope 24 and members 25 and 30, including the resilient prongs 31, will be integrally formed by molding.

Although the foregoing description has related primarily to measurement of uterine pressure, the invention may be employed to measure fluid pressure in various bodily cavities including blood vessels, as for example, to measure blood pressure.

What is claimed is:

1. Apparatus for use in measuring the pressure within a body cavity comprising:
    an elongated flexible catheter filled with liquid and having a gauge end adapted to be connected to a transducer and a perforated body end adapted to be inserted into said body cavity; a pressure sensitive diaphragm sealing the gauge end to said catheter;
    a guide tube filled with liquid and adapted to define a path within the body through which said catheter is to be advanced, said guide tube being less flexible and substantially shorter than said catheter, the perforated portion of said catheter being positioned within said guide tube, said guide tube including parallel score lines running the full length of said guide tube to thereby prescribe a fluid-tight but removable portion of the guide tube wall which can be removed to permit said catheter to be passed through said guide tube wall for separating said catheter and guide tube, a manually engageable member connected to said portion to enable said portion to be removed from said guide tube wall; and
    means releasably securing said catheter in a fixed relationship to said guide tube.

2. Apparatus according to claim 1 further comprising an envelope encasing said guide tube, said envelope having a selectively sealable fluid tight opening from which the gauge end of said catheter extends.

3. Apparatus according to claim 2 further comprising a compressible member disposed at the gauge end of said envelope and circumscribing said catheter and said securing means to form a fluid-tight seal at the gauge end of said envelope.

4. Apparatus according to claim 1, including means for sealing both ends of said guide tube.

5. As an article of manufacture for use in measuring intrauterine pressure, the combination comprising:
    an hollow elongated catheter filled with liquid and having a gauge end adapted to be connected to a transducer and a perforated uterine end adapted to be inserted into a patient's uterus;
    a pressure transmitting diaphragm sealing the gauge end of said catheter;
    a curved, fluid-tight guide tube filled with liquid and adapted to be inserted into the vaginal canal, said guide tube being shorter and less flexible than said catheter, the forward portion of said catheter being positioned within said guide tube, the uterine end of said guide tube including a weakened portion whereby said catheter can be axially forced through said uterine end to extend therebeyond, said guide tube also being scored along two lines throughout its length;
    a sleeve including a tab affixed to the gauge end of said guide tube at a region between said score lines whereby said tab may be grasped and pulled away from said guide tube thereby causing the wall portion of said guide tube between said score lines to be separated from the remainder of said guide tube, said sleeve releasably grasping an adjacent portion of said catheter;
    an outer envelope encasing said guide tube and filled with liquid, said envelope having a sealable opening for permitting said envelope, guide tube and catheter to be filled with a liquid and thereafter sealed; and
    means for selectively sealing said sealable opening.

6. An article of manufacture according to claim 5, wherein said means for selectively sealing comprises:
    a plug enveloping said catheter; yieldable prongs extending upwardly from the end of said envelope adjacent said plug; and
    an annular member for urging said prongs against said plug.

7. An article of manufacture according to claim 6, wherein said plug is slit longitudinally and engages at least a portion of said sleeve which grasps said catheter.

8. An article of manufacture according to claim 8, including a connector assembly secured to the gauge end of said catheter for connecting said catheter to a pressure transducer, said diaphragm being mounted in said connector assembly.

* * * * *